(12) United States Patent
Okazoe et al.

(10) Patent No.: US 6,858,752 B2
(45) Date of Patent: Feb. 22, 2005

(54) PROCESS FOR PRODUCING FLUORINATED POLYVALENT CARBONYL COMPOUND

(75) Inventors: Takashi Okazoe, Yokohama (JP); Kunio Watanabe, Yokohama (JP); Daisuke Shirakawa, Yokohama (JP); Masahiro Ito, Yokohama (JP); Shin Tatematsu, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 10/397,230

(22) Filed: Mar. 27, 2003

(65) Prior Publication Data

US 2003/0166969 A1 Sep. 4, 2003

Related U.S. Application Data

(63) Continuation of application No. PCT/JP01/08255, filed on Sep. 21, 2001.

(30) Foreign Application Priority Data

Sep. 27, 2000 (JP) ........................................ 2000-294801

(51) Int. Cl.[7] .............................................. C07C 69/63
(52) U.S. Cl. ...................... 560/227; 560/229; 560/226; 570/123; 570/124
(58) Field of Search ................................ 560/129, 226, 560/227, 229, 174, 190, 192; 570/101, 123, 124

(56) References Cited

U.S. PATENT DOCUMENTS 3,900,372 A    8/1975   Childs et al.
5,093,432 A    3/1992   Bierschenk et al.
5,322,903 A    6/1994   Bierschenk et al.
5,466,877 A    11/1995   Moore
6,255,536 B1    7/2001   Worm et al.

FOREIGN PATENT DOCUMENTS

| EP | 0 062 430 | 10/1982 |
| EP | 0 150 618 | 8/1985 |
| JP | 2-311438 | 12/1990 |
| JP | 2001-139509 | 5/2001 |
| WO | WO 95/25082 | 9/1995 |
| WO | WO 00/56694 | 9/2000 |
| WO | WO 02/10107 | 2/2002 |
| WO | WO 02/055471 | 7/2002 |

*Primary Examiner*—Johann Richter
*Assistant Examiner*—Karl Puttlitz
(74) *Attorney, Agent, or Firm*—Oblon, Spivak, McClelland, Maier & Neustadt, P.C.

(57) ABSTRACT

A fluorinated polyvalent carbonyl compound is produced by an economically advantageous method from inexpensive materials without requiring a complicated synthetic process step. Namely, the present invention comprises reacting a polyvalent alcohol having at least two kinds of alcohol skeletons selected among a primary alcohol, a secondary alcohol and a tertiary alcohol, with an acid halide to obtain a polyvalent ester compound, fluorinating it in a liquid phase to obtain a perfluorinated polyvalent ester compound, and cleaving the ester bonds derived from primary and secondary alcohols in the perfluoropolyvalent ester compound to obtain a fluorinated polyvalent carbonyl compound.

6 Claims, No Drawings

PROCESS FOR PRODUCING FLUORINATED POLYVALENT CARBONYL COMPOUND

TECHNICAL FIELD

The present invention relates to a process for producing a fluorinated polyvalent carbonyl compound and a novel fluorinated polyvalent carbonyl compound.

BACKGROUND ART

A fluorinated carbonyl compound such as an acyl fluoride, a perfluoroketone or a perfluoroester, is a compound highly useful as e.g. an intermediate for preparation of various fluorinated compounds. Especially, a fluorinated polyvalent carbonyl compound having at least two types of structures among the above-mentioned three types of structures, in one molecule, is very useful for the preparation of a fluorinated compound having a plurality of functional groups.

A method for obtaining a perfluoroacyl fluoride and a perfluoroketone by fluorinating an acid halide and a ketone having respectively corresponding structures by an electrochemical fluorination method (hereinafter referred to as "an ECF method"), or a method for obtaining them by pyrolyzing the ester bonds in perfluorinated alkyl ester compounds, has been known (see e.g. J. Am. Chem. Soc., 120, 7117 (1998)).

However, in a case where a fluorinated polyvalent carbonyl compound is to be produced by the above prior art method, a polyvalent alkyl ester compound as a raw material for a perfluoropolyvalent alkyl ester compound to be pyrolyzed, is not readily available, and many complicated synthetic process steps will be required, whereby there have been problems such that the price of the perfluoropolyvalent alkyl ester compound is high, and available compounds are rather limited. Further, the prior art method has had a problem that the yield in the reaction for the synthesis is low.

DISCLOSURE OF THE INVENTION

The present invention has been made in view of the above-mentioned problems of the prior art and is intended to provide a process for producing a fluorinated polyvalent carbonyl compound economically advantageously from materials which are inexpensively available, without requiring a complicated synthetic step.

The present inventors have conducted an extensive study to accomplish the above object and as a result, have found it possible to obtain a fluorinated polyvalent carbonyl compound without requiring a complicated synthetic step, by a process wherein a polyvalent alcohol having at least two types of alcohol skeletons among a primary alcohol, a secondary alcohol and a tertiary alcohol, is used as a starting material, and the polyvalent alcohol and an acid halide are reacted to obtain a polyvalent ester compound, which is fluorinated by a specific fluorination method, followed by cleaving the specific ester bonds. Further, it has been found that the above process is an economically advantageous industrial production process, since the polyvalent alcohol is available inexpensively in various structures, and the present invention has been accomplished.

Namely, the present invention provides the following invention.

(a) A process for producing a compound of the following formula (5), which comprises reacting a compound of the following formula (1) with a compound of the following formula (2) to obtain a compound of the following formula (3), then reacting the compound of the following formula (3) with fluorine in a liquid phase to obtain a compound of the following formula (4), and further cleaving the ester bonds derived from the primary and secondary alcohols in the compound of the formula (4):

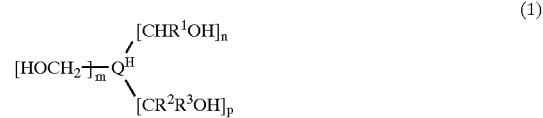

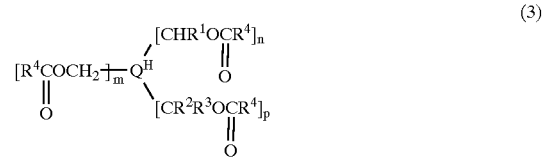

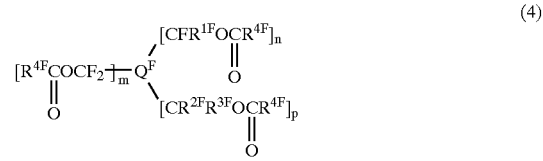

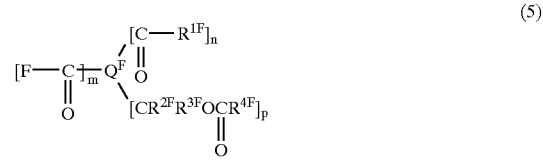

wherein each of $R^1$, $R^2$, $R^3$ and $R^4$ which may be the same or different, is a monovalent organic group; $Q^H$ is a (m+n+p)valent organic group; $R^{1F}$, $R^{2F}$, $R^{3F}$, $R^{4F}$ and $Q^F$ are the same groups as $R^1$, $R^2$, $R^3$, $R^4$ and $Q^H$, respectively, or groups having $R^1$, $R^2$, $R^3$, $R^4$ and $Q^H$ fluorinated, respectively; X is a halogen atom; otherwise, $R^2$ and $R^3$, or $R^{2F}$ and $R^{3F}$, may, respectively, be connected to constitute a bivalent group; each of m, n and p is an integer of at least 0, provided that (m+n+p)≧2, and n and p are not 0 at the same time, and when m is 1, n is 1, and p is 0, or when m is 1, n is 0, and p is 1, $Q^H$ may be a single bond, and when $Q^H$ is a single bond, $Q^F$ is a single bond.

(b) The process wherein a compound of the following formula (6) is obtained, together with the compound of the formula (5), from the reaction product obtained by cleaving the ester bonds derived from the primary and secondary alcohols in the compound of the formula (4):

wherein $R^{4F}$ is as defined above.

(c) The process wherein the compound of the formula (2) has the same structure as the compound of the formula (6), and at least a part of the compound of the formula (6) obtained from the reaction product obtained by cleaving the ester bonds in the compound of the formula (4) is used as at least a part of the compound of the formula (2) to be reacted with the compound of the formula (1), so that the compound of the formula (5) can be obtained continuously (d) A compound of the following formula (7), a compound of the following formula (8), a compound of the following formula (9), a compound of the following formula (1-1a) or a compound of the following formula (1-1b):

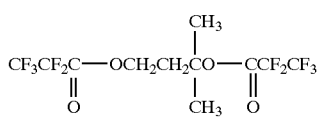   (7)

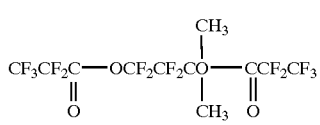   (8)

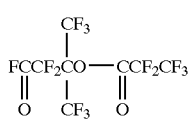   (9)

CH₃CH[OCOCF(CF₃)OCF₂CF(CF₃)OCF₂CF₂CF₃]
CH₂OCOCF(CF₃)OCF₂CF(CF₃)OCF₂CF₂CF₃   (1-1a)

CF₃CF[OCOCF(CF₃)OCF₂CF(CF₃)OCF₂CF₂CF₃]
CF₂OCOCF(CF₃)OCF₂CF(CF₃)OCF₂CF₂CF₃   (1-1b)

BEST MODE FOR CARRYING OUT THE INVENTION

In this specification, a compound of the formula (1) will be represented by a compound (1). Compounds of other formulae will be represented similarly. In the present invention, firstly, a step (hereinafter referred to as "an esterification step") of reacting the compound (1) with the compound (2) to obtain a compound (3), is carried out.

The compound (1) to be used in the esterification step is a polyvalent alcohol having a structure in which m in number of —CH₂OH, n in number of —CHR¹OH and p in number of —CR²R³OH being monovalent groups, are bonded to $Q^H$. These monovalent groups are bonded to the same carbon atom or different carbon atoms in $Q^H$, so that $Q^H$ will be a (m+n+p)valent organic group. Otherwise, when m is 1, n is 1 and p is 0, $Q^H$ may be a single bond. The compound (1) in such a case is the following compound (1-1) having a group of —CH₂OH and a group of —CHR¹OH connected. Otherwise, when m is 1, n is 0 and p is 1, $Q^H$ may be a single bond. The compound (1) in such a case is the following compound (1-2) having a group of —CH₂OH and a group of —CR²R³OH connected. Here, R¹, R² and R³ in the following formulae are as defined above.

HOCH₂CHR¹OH   (1-1)

HOCH₂CR²R³OH   (1-2)

In the above monovalent groups, each of R¹, R² and R³ which may be the same or different, is a monovalent organic group. The monovalent organic group may, for example, be a monovalent hydrocarbon group, a monovalent halogenated hydrocarbon group, a monovalent hetero atom-containing hydrocarbon group or a monovalent halogenated (hetero atom-containing hydrocarbon) group. In the present invention, each of R¹, R² and R³ which may be the same or different, is preferably a monovalent saturated organic group having hydrogen atoms.

Here, the organic group, the hydrocarbon group, the halogenated hydrocarbon group, the hetero atom-containing hydrocarbon group and the halogenated (hetero atom-containing hydrocarbon) group are groups which will be defined hereinafter. In the present invention, the following definitions will be used consistently even in such a case that the types of compounds having these groups are different.

The organic group is a group containing at least one carbon atom, and the hydrocarbon group is an organic group comprising carbon atoms and hydrogen atoms. Further, the halogenated hydrocarbon group means a hydrocarbon group wherein at least one hydrogen atom bonded to a carbon atom is substituted by a halogen atom. The hetero atom-containing hydrocarbon group is a hydrocarbon group containing a hetero atom (an oxygen atom, a nitrogen atom, a sulfur atom or the like) and/or a hetero atom group (such as —C—C(=O)—C— or —C—SO₂—C—). Further, the halogenated (hetero atom-containing hydrocarbon) group is a group having at least one hydrogen atom bonded to a carbon atom in the above hetero atom-containing hydrocarbon group, substituted by a halogen atom. Further, in the present invention, a group wherein carbon-carbon bonds are solely single bonds, is identified by putting "saturated" before the name of the group. A "saturated" group may contain an unsaturated bond, so long as the carbon-carbon bonds in that group are single bonds.

Further, in the present invention, a group having at least one hydrogen atom bonded to a carbon atom substituted by a halogen atom, is identified by putting "halogenated" before the name of the group. Especially, a group having substantially all hydrogen atoms bonded to carbon atoms substituted by halogen atoms, is identified by putting "perhalogenated" before the name of the group. On the other hand, a group having part of hydrogen atoms bonded to carbon atoms is substituted by a halogen atom is identified by putting "partially halogenated" before the name of the group. In these groups, when the halogen atom is specified, for example, when the halogen atom is a fluorine atom, "perfluoro", "partially fluoro" or the like will be put. Further, halogen atoms in the "perhalogenated" group and the "partially halogenated" group, may be of one type or two or more types.

Further, the "perhalogenated" group is preferably a group having all hydrogen atoms bonded to carbon atoms substituted by halogen atoms, but even in a case where unsubstituted hydrogen atoms still remain, so long as the nature as a group is substantially equal to a "perhalogenated" group, such a group is included in the concept of the "perhalogenated" group in the present invention.

In a case where R¹, R² or R³ in the compound (1) is a monovalent hydrocarbon group, the carbon number is preferably from 1 to 20, more preferably from 1 to 10. The monovalent hydrocarbon group may, for example, be a monovalent aliphatic hydrocarbon group such as an alkyl group, a monovalent alicyclic hydrocarbon group such as a cycloalkyl group or a cycloalkylalkyl group, or a monovalent aromatic hydrocarbon group such as a phenyl group, preferably a monovalent aliphatic hydrocarbon group, more preferably an alkyl group. In the monovalent aliphatic hydrocarbon group, a single bond, a double bond or a triple bond may be present as a carbon-carbon bond. Further, the structure of such a group may be a straight chain structure, a branched structure, a cyclic structure or a structure partially having a cyclic structure.

The alkyl group is preferably a C₁₋₁₀ alkyl group, particularly preferably a methyl group, an ethyl group or a propyl group. The cycloalkyl group is preferably a cycloalkyl group of from 3- to 6-membered ring or a group having at least one hydrogen atom of such a cycloalkyl group substituted by an alkyl group. The cycloalkylalkyl group is preferably a group having one hydrogen atom in a $C_{1-3}$ alkyl group substituted by a cycloalkyl group, and as such a group, a cyclohex methyl group may, for example, be mentioned.

In a case where $R^1$, $R^2$ or $R^3$ in the compound (1) is a monovalent halogenated hydrocarbon group, the type of the halogen atom is not particularly limited, and a fluorine atom or a chlorine atom is preferred. The monovalent halogenated hydrocarbon group may, for example, be a fluoroalkyl group or a fluorochloroalkyl group. Further, the carbon number of the monovalent halogenated hydrocarbon group is preferably from 1 to 20, more preferably from 1 to 10.

The monovalent halogenated hydrocarbon group may be a monovalent perhalogenated hydrocarbon group or a monovalent partially halogenated hydrocarbon group, and its structure may be a straight chain structure, a branched structure or a structure partially having a cyclic structure. Further, such a group is preferably a saturated group.

The monovalent perhalogenated hydrocarbon group is preferably a perfluoroalkyl group or a perfluoro(partially chloroalkl) group which is a group having substantially all hydrogen atoms in a partially chlorinated alkyl group substituted by fluorine atoms.

In a case where $R^1$, $R^2$ or $R^3$ in the compound (1) is a monovalent hetero atom-containing hydrocarbon group, the carbon number is preferably from 1 to 20, more preferably from 1 to 10. The hetero atom in such a group is preferably an etheric oxygen atom (—O—) or =O. Further, the hetero atom may be in the form of a hetero atom group, and as such a hetero atom group, —C—C(=O)—C— or —C—SO$_2$—C— is preferred.

The hetero atom and The hetero atom group are preferably those which undergo no change by pyrolysis and/or a fluorination reaction. Particularly preferred is an etheric oxygen atom. Further, as the hetero atom group, —C—C(=O)—C— or —C—SO$_2$—C— is preferred.

The monovalent hetero atom-containing hydrocarbon group is preferably an etheric oxygen atom-containing alkyl group, particularly preferably an alkoxyalkyl group, from the viewpoint of availability, production efficiency and usefulness of the product.

In a case where $R^1$, $R^2$ or $R^3$ in the compound (1) is a monovalent halogenated (hetero atom-containing hydrocarbon) group, it is preferably a group having at least one hydrogen atom bonded to a carbon atom in the above monovalent hetero atom-containing hydrocarbon group substituted by a halogen atom. Here, the type of the halogen atom is not particularly limited, and a fluorine atom or a chlorine atom is preferred.

The monovalent halogenated (hetero atom-containing hydrocarbon) group may, for example, be a fluoro(hetero atom-containing hydrocarbon) group or a fluorochloro (hetero atom-containing hydrocarbon) group. Further, the carbon number of the monovalent halogenated (hetero atom-containing hydrocarbon) group is not particularly limited, and it is preferably from 1 to 20, more preferably from 1 to 10.

The monovalent halogenated (hetero atom-containing hydrocarbon) group may be a monovalent perhalogenated (hetero atom-containing hydrocarbon) group or a monovalent partially halogenated (hetero atom-containing hydrocarbon) group. The perhalogenated group is preferably a monovalent perfluoro(hetero atom-containing hydrocarbon) group or a monovalent perfluoro(partially chlorinated (hetero atom-containing hydrocarbon)) group. Further, the monovalent halogenated (hetero atom-containing hydrocarbon) group is preferably a saturated group, and its structure may be a straight chain structure, a branched structure or a structure partially having a cyclic structure.

The monovalent halogenated (hetero atom-containing saturated hydrocarbon) group is preferably a fluoro (alkoxyalkyl) group or a fluorochloro(alkoxyalkyl) group, and the monovalent perhalogenated (hetero atom-containing saturated hydrocarbon) group is preferably a perfluoro (alkoxyalkyl) group or a perfluoro(partially chlorinated (alkoxyalkyl)) group.

$R^2$ and $R^3$ in the compound (1) to be used in the esterification step, may be connected to form a bivalent group. Such a bivalent group may be a bivalent organic group such as a bivalent hydrocarbon group, a bivalent halogenated hydrocarbon group, a bivalent hetero atom-containing hydrocarbon group or a bivalent halogenated (hetero atom-containing hydrocarbon) group. Such a bivalent organic group is preferably a group having one hydrogen atom or one halogen atom present in the above-mentioned group such as a monovalent hydrocarbon group, a monovalent halogenated hydrocarbon group, a monovalent hetero atom-containing hydrocarbon group or a monovalent halogenated (hetero atom-containing hydrocarbon) group converted to a connecting bond. The type or combination of preferred halogen atoms, hetero atoms or hetero atom groups in such a bivalent group, is the same as described above. Further, the carbon number of the bivalent group is preferably from 2 to 40, more preferably from 2 to 20, further preferably from 2 to 10.

The bivalent hydrocarbon group may, for example, be a straight chain alkylene group, a branched alkylene group or a cycloalkylene group, and the bivalent halogenated hydrocarbon group may, for example, be a group having some or all of hydrogen atoms bonded to carbon atoms in the above-mentioned bivalent hydrocarbon group substituted by fluorine atoms and at least one type of halogen atoms other than fluorine atoms (preferably chlorine atoms).

Further, the bivalent hetero atom-containing hydrocarbon group may, for example, be a group having from 1 to 6 (preferably from 1 to 3) etheric oxygen atoms inserted between carbon-carbon bonds of the above-mentioned bivalent hydrocarbon group.

Further, the bivalent halogenated (hetero atom-containing hydrocarbon) group may, for example, be a group having some or all of hydrogen atoms bonded to carbon atoms in a bivalent hetero atom-containing hydrocarbon group substituted by fluorine atoms or at least one type of halogen atoms other than fluorine atoms (preferably chlorine atoms). As such a group, preferred is a fluorochloro(etheric oxygen atom-containing alkylene) group, a perfluoro(etheric oxygen atom-containing alkylene) group or a perfluoro(partially chlorinated (etheric oxygen atom-containing alkylene)) group.

$Q^H$ in the compound (1) is a (m+n+p)valent organic group, and such an organic group is preferably a hydrocarbon group, a halogenated hydrocarbon group, a hetero atom-containing hydrocarbon group or a halogenated (hetero atom-containing hydrocarbon) group. Further, $Q^H$ is preferably a (m+n+p)valent saturated organic group having hydrogen atoms. Such a saturated organic group is preferably a saturated hydrocarbon group or a hetero atom-containing saturated hydrocarbon group.

The hetero atom in the (m+n+p)valent hetero atom-containing saturated hydrocarbon group, is the same as described above, and it is preferably one which undergoes no change by pyrolysis and/or a fluorination reaction, and an etheric oxygen atom is preferred. Further, it may be a group which contains a hetero atom group such as —C—C(=O)—C— or —C—SO$_2$—C—.

The structure of $Q^H$ may be a straight chain structure, a branched structure, a cyclic structure or a structure partially having a cyclic structure. Further, the carbon number of $Q^H$ is preferably from 1 to 20, particularly preferably from 1 to 10.

Further, in a case where m is 1, n is 1 and p is 0, or in a case where m is 1, n is 0 and p is 1, $Q^H$ may be a bivalent organic group or a single bond.

The compound (1) to be used in the esterification step, is a polyvalent alcohol having a structure in which m in number of —CH$_2$OH group, n in number of —CHR$^1$OH group and p in number of —CR$^2$R$^3$OH group, are bonded to $Q^H$. Or, the compound (1) is, the above compound (1-1) or the above compound (1-2), a bihydric alcohol wherein one of the terminals is a primary hydroxyl group, and the other terminal is a secondary hydroxyl group or a tertiary hydroxyl group.

The compound (3) formed by the reaction of the compound (1) with the compound (2), is then reacted with fluorine in a liquid phase. To improve the solubility of the compound (3) in the liquid phase for this purpose, the compound preferably has a structure containing halogen atoms (preferably fluorine atoms). Accordingly, at least one of R$^1$, R$^2$, R$^3$, R$^4$ and $Q^H$ in the compound (3) is preferably a group containing halogen atoms (preferably fluorine atoms). Further, in order to efficiently obtain the fluorinated polyvalent carbonyl compound of the present invention at a low cost, it is preferred to employ as the compound (1) a compound containing no halogen atoms such as fluorine atoms and to employ as the compound (2) one containing halogen atoms such as fluorine atoms. Accordingly, R$^1$, R$^2$ or R$^3$ in the compound (1) is particularly preferably a monovalent hydrocarbon group such as an alkyl group or a monovalent hetero atom-containing hydrocarbon group such as an alkoxy group or an alkoxyalkyl group, among the above-mentioned monovalent organic groups, and $Q^H$ is particularly preferably a (m+n+p)valent saturated hydrocarbon group. R$^1$, R$^2$ or R$^3$ is most preferably an alkyl group. Further, in the compound (1), it is preferred that m is an integer of at least 1, n is an integer of at least 0, and p is an integer of at least 1. Further, m in the compound (1) is more preferably an integer of from 1 to 10, further preferably 1 or 2. n is more preferably an integer of from 0 to 10, particularly preferably an integer of from 0 to 2. p is more preferably an integer of from 0 to 10, particularly preferably integer of from 0 to 2.

Further, in the compound (1), it is also preferred that m is an integer of at least 1, n is an integer of at least 1, and p is an integer of at least 0.

Further, in a case where m is 1, n is 1 and p is 0, or in a case where m is 1, n is 0 and p is 1, each of R$^1$, R$^2$ and R$^3$ in a case where $Q^H$ is a single bond, is preferably an alkyl group, particularly preferably a methyl group.

In the esterification step, the compound (1) and the compound (2) are reacted.

In the compound (2), R$^4$ is a monovalent organic group, and the monovalent organic group may, for example, be a monovalent hydrocarbon group, a monovalent halogenated hydrocarbon group, a monovalent hetero atom-containing hydrocarbon group or a monovalent halogenated (hetero atom-containing hydrocarbon) group. The definitions and specific examples for the monovalent hydrocarbon group, the monovalent halogenated hydrocarbon group, the monovalent hetero atom-containing hydrocarbon group and the monovalent halogenated (hetero atom-containing hydrocarbon) group, are as described above.

As mentioned above, from the viewpoint of the economical efficiency and availability of starting materials, R$^4$ in the compound (2) is preferably a monovalent organic group containing halogen atoms (preferably fluorine atoms). R$^4$ is more preferably a monovalent perhalogenated organic group, particularly preferably a monovalent perfluorinated organic group. Namely, R$^4$ is preferably a monovalent perfluorinated saturated hydrocarbon group, a monovalent perfluoro(partially chlorinated saturated hydrocarbon) group, a monovalent perfluoro(hetero atom-containing saturated hydrocarbon) group or a monovalent perfluoro (partially chlorinated (hetero atom-containing saturated hydrocarbon)) group.

In the compound (2), X is a halogen atom. The halogen atom may be a fluorine atom, a chlorine atom, a bromine atom or an iodine atom. Among them, a fluorine atom, a chlorine atom or a bromine atom is preferred, and a fluorine atom or a chlorine atom is more preferred. A fluorine atom is particularly preferred.

The reaction of the compound (1) and the compound (2) can be carried out under the conditions for a known esterification reaction. The reaction may be carried out in the presence of a solvent (hereinafter referred to as "solvent 1"), but it is preferred to carry out the reaction in the absence of solvent 1, from the viewpoint of the volume efficiency. In a case where solvent 1 is employed, dichloromethane, chloroform, triethylamine or a mixed solvent of triethylamine and tetrahydrofuran, is preferred. The amount of solvent 1 to be used is preferably from 50 to 500 mass %, based on the total amount of the compound (1) and the compound (2).

By the reaction of the compound (1) and the compound (2), an acid represented by HX will be generated. In a case where a compound wherein X is a fluorine atom, is employed as the compound (2), HF will be generated, and as a HF scavenger, an alkali metal fluoride (preferably NaF or KF) or a trialkylamine may be permitted to be present in the reaction system. In a case where the compound (1) or the compound (2) is a compound unstable against an acid, it is preferred to use a scavenger for HF. Further, in a case where no HF scavenger is used, it is preferred to discharge HF out of the reaction system, as accompanied by a nitrogen stream. In a case where an alkali metal fluoride is employed, its amount is preferably from 1 to 10 mols per mol of the compound (2).

The temperature for the reaction of the compound (1) and the compound (2) is preferably at least −50° C. and preferably at most the boiling point of the solvent and at most +100° C. Further, the reaction time for the reaction may suitably be changed depending upon the supply rates of the starting materials and the amounts of the compounds to be used for the reaction. The pressure for the reaction (gauge pressure, the same applies hereinafter) is preferably from atmospheric pressure to 2 MPa. The compound (3) to be formed by the reaction of the compound (1) and the compound (2) is preferably a compound which is readily soluble in a liquid phase when the after-mentioned fluorination is carried out in the liquid phase and which has a molecular weight sufficient to prevent the decomposition reaction. Namely, the molecular weight of the compound (3) is preferably from 200 to 1,000. If the molecular weight is less than 200, the compound (3) tends to be vaporized, whereby during the fluorination reaction in a liquid phase, a decomposition reaction in a gas phase is likely to take place. On the other hand, if the molecular weight exceeds 1,000, purification of the compound (3) tends to be difficult.

Further, in a case where the compound (3) is a fluorinated compound, the fluorine content in the compound (3) (the proportion of fluorine atoms in the molecule) is preferably suitably changed depending upon the type of the aftermentioned liquid phase. Usually, the fluorine content is preferably at least 30 mass %, more preferably from 30 to 86 mass %, further preferably from 30 to 76 mass %.

The crude product containing the compound (3) formed by the reaction of the compound (1) and the compound (2), may be purified depending upon the particular purpose or may be used for e.g. the subsequent reaction as it is. It is advisable to purify the crude product so that the fluorination reaction in the next step can be proceeded smoothly.

As the method for purifying the crude product, a method of distilling the crude product as it is, a method of treating the crude product with a dilute alkali aqueous solution, followed by liquid separation, a method of extracting the crude product with a suitable organic solvent, followed by distillation, or silica gel column chromatography, may, for example, be mentioned.

Then, a step (hereinafter referred to as a "fluorination step") of reacting the above compound (3) with fluorine in a liquid phase to obtain a compound (4), is carried out. The fluorination reaction in the fluorination step is carried out in a liquid phase from the viewpoint of the operation efficiency for the reaction and the yield. Such a fluorination reaction can be theoretically carried out even by an ECF method, a cobalt fluorination method or a method of reacting it with fluorine in a gas phase, but fluorination in a liquid phase is a remarkably advantageous method from the viewpoint of e.g. the yield and the operation efficiency of the reaction.

The fluorination reaction can be carried out by a method wherein the compound (3) and fluorine ($F_2$) are reacted in the presence of a solvent (hereinafter referred to as "solvent 2") to obtain a compound (4). Such a method is a method so-called liquid phase fluorination. As the fluorine, fluorine gas may be used as it is, or fluorine gas diluted with an inert gas, may be employed. As such an inert gas, nitrogen gas or helium gas is preferred, and from the economical reason, nitrogen gas is particularly preferred. The amount of fluorine in the inert gas such as nitrogen gas, is not particularly limited, and it is preferably at least 10 vol % from the viewpoint of the efficiency, particularly preferably at least 20 vol %.

Solvent 2 is preferably a solvent which contains no C—H bond and which essentially contains a C—F bond, and it is further preferably a perfluoroalkane or an organic solvent obtained by perfluorinating a known organic solvent containing in its structure at least one type of atom selected from the group consisting of a chlorine atom, a nitrogen atom and an oxygen atom. Further, as solvent 2, it is preferred to employ a solvent which dissolves the compound (3) with a high solubility, specifically a solvent which is capable of dissolving at least 1 mass % of the compound (3), particularly preferably a solvent capable of dissolving at least 5 mass % thereof.

As an example of solvent 2, a compound of the following formula (6), a perfluoroalkane (such as FC-72, tradename), a perfluoroether (such as FC-75 or FC-77), a perfluoropolyether (such as Krytox, Fonbrine, Garden or Demnum, tradename), a chlorofluorocarbon (Flonrube, tradename), a chlorofluoropolyether, a perfluoroalkylamine (such as a perfluorotrialkylamine), or an inert fluid (Florinate, tradename) may, for example, be mentioned. Among them, a perfluorotrialkylamine or a compound (6) is preferred. Especially when the compound (6) is employed, post treatment after the reaction can be facilitated, such being advantageous. The amount of solvent 2 is preferably at least 5 times by mass, particularly preferably from 10 to 100 times by mass, based on the compound (3).

The reaction system or the fluorination reaction may be a batch system or a continuous system. Further, the fluorination reaction is preferably carried out by the following fluorination method 1 or 2, and from the viewpoint of the yield and selectivity in the reaction, it is preferred to carry out the reaction by fluorination method 2. Further, as the fluorine gas, one diluted with an inert gas such as nitrogen gas may be used either in a case where the reaction is carried out by a batch system or in a case where the reaction is carried out by a continuous system.

Fluorination Method 1

A method which comprises charging the compound (3) and solvent 2 into a reactor, initiating stirring, controlling the temperature and pressure to the prescribed reaction temperature and reaction pressure, and then continuously supplying fluorine gas, or fluorine gas and solvent 2, to carry out the reaction.

Fluorination Method 2

A method which comprises charging solvent 2 into a reactor, initiating stirring, controlling the temperature and pressure to the prescribed reaction temperature and reaction pressure, and then continuously and simultaneously supplying the compound (3) and fluorine gas at a prescribed molar ratio.

When the compound (3) is supplied in the continuous system 2, it is preferred to supply the compound (3) diluted with solvent 2, in order to improve the selectivity and to suppress the amount of by-products. Further, when the compound (3) is diluted with the solvent in the continuous system 2, the amount of solvent 2 to the compound (3) is adjusted to be preferably at least 5 times by mass, particularly preferably at least 10 times by mass.

The amount of fluorine to be used for the fluorination reaction is preferably adjusted to be such an amount that the amount of fluorine will be always in excess equivalent to the hydrogen atoms to be fluorinated in either case of carrying out the reaction by a batch system or by a continuous system, and it is particularly preferably adjusted to be at least 1.5 times by equivalent (i.e. at least 1.5 mols) to the hydrogen atoms, from the viewpoint of the selectivity. The amount of fluorine is preferably maintained to be always in excess equivalent from the initiation of the reaction to the end of the reaction.

The reaction temperature for the fluorination reaction is usually preferably at least −60° C. and at most the boiling point of the compound (3), and from the viewpoint of the yield, selectivity and industrial applicability of the reaction, it is particularly preferably from −50° C. to +100° C., especially preferably from −20° C. to +50° C. The reaction pressure for the fluorination reaction is not particularly limited, and it is particularly preferably from atmospheric pressure to 2 MPa from the viewpoint of the yield, selectivity and industrial applicability of the reaction.

Further, in order to have the fluorination reaction proceeded efficiently, it is preferred to add a C—H bond-containing compound to the reaction system or to carry out ultraviolet ray irradiation, at a later stage of the reaction. For example, it is preferred that at a later stage of the fluorination reaction, a C—H bond-containing compound is added to the reaction system, or ultraviolet ray irradiation is carried out. By the use of a C—H bond-containing compound, the compound (3) present in the reaction system can efficiently be fluorinated, whereby the conversion can remarkably be improved.

The C—H bond-containing compound is an organic compound other than the compound (3), particularly preferably an aromatic hydrocarbon, especially preferably benzene, toluene or the like. The amount of the C—H bond-containing compound to be added, is preferably from 0.1 to 10 mol %, particularly preferably from 0.1 to 5 mol %, based on hydrogen atoms in the compound (3).

The C—H bond-containing compound is preferably added in a state where fluorine gas is present in the reaction system. Further, when a C—H bond-containing compound is added, the reaction system is preferably pressurized. The pressure for pressurizing is preferably from 0.01 to 5 MPa.

By the fluorination step, the compound (3) is fluorinated to form a compound (4). In the compound (4), $R^{1F}$ corresponds to $R^1$, $R^{2F}$ corresponds to $R^2$, $R^{3F}$ corresponds to $R^3$, $R^{4F}$ corresponds to $R^4$, and $Q^F$ correspond to $Q^H$. In a case where $R^1$, $R^2$, $R^3$, $R^4$ and $Q^H$ are groups to be fluorinated, respectively, and have been actually fluorinated, $R^{1F}$, $R^{2F}$, $R^{3F}$, $R^{4F}$ and $Q^F$ are groups having $R^1$, $R^2$, $R^3$, $R^4$ and $Q^H$ fluorinated, respectively. For example, in a case where $R^1$, $R^2$, $R^3$, $R^4$ and $Q^H$ are groups containing hydrogen atoms, if they are fluorinated, $R^{1F}$, $R^{2F}$, $R^{3F}$, $R^{4F}$ and $Q^F$ are groups having at least one hydrogen atom in $R^1$, $R^2$, $R^3$, $R^4$ and $Q^H$ substituted by a fluorine atom. Further, in a case where a —CH=CH— portion or a —C≡C— portion is present in $R^1$, $R^2$, $R^3$, $R^4$ or $Q^H$, fluorine atoms may be added to such a portion by the fluorination step to form —$CF_2CF_2$—. On the other hand, in a case where $R^1$, $R^2$, $R^3$, $R^4$ and $Q^H$ are groups not fluorinated, or even if they are groups which can be fluorinated, if they are not fluorinated, $R^{1F}$, $R^{2F}$, $R^{3F}$, $R^{4F}$ and $Q^F$ are the same groups as $R^1$, $R^2$, $R^3$, $R^4$ and $Q^H$, respectively. In the fluorination reaction in the liquid phase in the present invention, hydrogen atoms bonded to carbon atoms in $R^1$, $R^2$, $R^3$, $R^4$ and $Q^H$, will be substituted by fluorine atoms, but chlorine atoms, bromine atoms or iodine atoms bonded to carbon atoms will not be substituted by fluorine atoms. Further, in a case where $Q^H$ is a single bond, $Q^F$ will be a single bond.

In the present invention, it is preferred that in the fluorination reaction, the compound (3) is perfluorinated. Further, $R^1$, $R^2$ and $R^3$ may be the same or different and are preferably a monovalent saturated organic group having hydrogen atoms. In such a case, $R^{1F}$, $R^{2F}$ and $R^{3F}$ are preferably a monovalent perfluorinated saturated organic group having all hydrogen atoms in said saturated organic group substituted by fluorine atoms. In the present invention, it is also preferred that $Q^H$ is a (m+n+p)valent saturate organic group having hydrogen atoms, and in such a case, $Q^F$ is preferably a (m+n+p)valent perfluorinated saturated organic group having all hydrogen atoms in $Q^H$ substituted by fluorine atoms.

The compound (3) wherein $R^1$, $R^2$, $R^3$, $R^4$ and $Q^H$ are a saturated hydrocarbon group, a halogenated saturated hydrocarbon group, a hetero atom-containing saturated hydrocarbon group or a halogenated (hetero atom-containing saturated hydrocarbon) group, is preferably such that all hydrogen atoms in such a group are substituted by fluorine atoms.

Accordingly, each of $R^{1F}$, $R^{2F}$, $R^{3F}$ and $R^{4F}$ is preferably a monovalent perfluoro saturated hydrocarbon group, a monovalent perfluoro(partially halogenated saturated hydrocarbon) group, a monovalent perfluoro(hetero atom-containing saturated hydrocarbon) group or a monovalent perfluoro(halogenated (hetero atom-containing saturated hydrocarbon)) group, and $Q^F$ is preferably a (m+n+p)valent perfluorinated saturated hydrocarbon group, a (m+n+p)valent perfluoro(partially halogenated saturated hydrocarbon) group, a (m+n+p)valent perfluoro(hetero atom-containing saturated hydrocarbon) group or a (m+n+p)valent perfluoro(partially halogenated (hetero atom-containing saturated hydrocarbon)) group.

In the compound (4), $R^{2F}$ and $R^{3F}$ may be connected to form a bivalent group. In the present invention, $R^2$ and $R^3$ which are not connected, will not be connected in the process of the above fluorination. Accordingly, a bivalent group having $R^{2F}$ and $R^{3F}$ connected to each other, is a group corresponding to a bivalent group having $R^2$ and $R^3$ connected to each other. Namely, a bivalent group having $R^{2F}$ and $R^{3F}$ connected to each other, is a group obtained by fluorination of a bivalent group having $R^2$ and $R^3$ connected to each other. Here, in a case where a bivalent group having $R^2$ and $R^3$ connected to each other, is a non-fluorinated group, the bivalent group having $R^{2F}$ and $R^{3F}$ connected to each other will be the same as the bivalent group having $R^2$ and $R^3$ connected to each other.

Such a bivalent group having $R^{2F}$ and $R^{3F}$ connected to each other, may, for example, be a bivalent perfluorinated saturated hydrocarbon group, a bivalent perfluoro(partially halogenated saturated hydrocarbon) group, a bivalent perfluoro(hetero atom-containing saturated hydrocarbon) group or a bivalent perfluoro(partially halogenated (hetero atom-containing saturated hydrocarbon)) group. Among them, a perfluoroalkylene group or a perfluoro(alkyleneoxyalkylene) group is preferred.

In a case where a reaction to substitute hydrogen atoms by fluorine atoms takes place in the reaction for fluorinating the compound (3) in a liquid phase, HF will be formed as a by-product. To remove the by-product HF, it is preferred to permit a HF scavenger to be present in the reaction system or to let the outlet gas contact with a HF scavenger at the gas outlet of the reactor. As such a HF scavenger, the same one as described above may be employed, and NaF is preferred.

The amount of the HF scavenger to be permitted to be present in the reaction system, is preferably from 1 to 20 times by mol, particularly preferably from 1 to 5 times by mol, based on the total amount of hydrogen atoms present in the compound (3). In a case where the HF scavenger is placed at the gas outlet of the reactor, it is preferred to arrange (a) a cooler (which is preferably maintained at from 10° C. to room temperature, particularly preferably at about 20° C.) (b) a layer packed with NaF pellets and (c) a cooler (which is preferably maintained at from −78° C. to +10° C., more preferably from −30° C. to 0° C.) in series in the order of (a)-(b)-(c). Further, a liquid returning line may be installed to return the condensed liquid from the cooler (c) to the reactor.

The crude product containing the compound (4) obtained in the fluorination step may be used as it is in the subsequent step or may be purified to be highly pure. The purification method may, for example, be a method of distilling the crude product as it is under normal pressure or reduced pressure.

Then, a step (hereinafter referred to as a "cleavage step") of cleaving-the ester bonds derived from the primary and secondary alcohols in the compound (4) to obtain a compound (5), is carried out.

The cleavage step is preferably carried out by a cleavage reaction which is carried out by a pyrolytic reaction or in the presence of a nucleophilic agent or an electrophilic agent.

The pyrolytic reaction can be carried out by heating the compound (4). As the reaction system for the pyrolytic reaction, it is preferred to select it depending upon the boiling point and the stability of the compound (4). For example, in a case where a readily vaporizable compound (4) is subjected to pyrolysis, it is possible to employ a gas phase pyrolytic method wherein the decomposition is carried out continuously in a gas phase, and an outlet gas containing the obtained compound (5) is condensed and recovered.

The reaction temperature for the gas phase pyrolysis is preferably from 50 to 350° C., more preferably from 50 to 300° C., particularly preferably from 150 to 250° C. Further, in the reaction, an inert gas which will not be involved directly in the reaction, may be present in the reaction system. As such an inert gas, nitrogen, or carbon dioxide may, for example, be mentioned. The inert gas is preferably added in an amount of from 0.01 to 50 vol %, based on the compound (4). If the amount of the inert gas added, is large, the amount of the product to be recovered may decrease.

On the other hand, in a case where the compound (4) is a compound which is hardly vaporized, it is preferred to adopt a liquid phase pyrolytic method wherein it is heated in the form of a liquid in the reactor. The reaction pressure in such a case is not particularly limited. In a usual case, the product containing the compound (5) has a low boiling point. Accordingly, it is preferably obtained by a method of a reaction distillation system wherein the product is vaporized and continuously withdrawn. Further, it may be a method wherein the product is withdrawn all at once from the reactor after completion of the heating. The reaction temperature for such a liquid phase pyrolysis is preferably from 50 to 300° C., particularly preferably 100 to 250° C.

The pyrolysis by a liquid phase pyrolytic method may be carried out in the absence or presence of a solvent (hereinafter referred to as "solvent 3"). Solvent 3 is not particularly limited so long as it does not react with the compound (4) and has a compatibility with the compound (4) and it is not reactive with the resulting compound (5). Further, as solvent 3, it is preferred to select one which can easily be separated at the time of purification of the compound (5). As a specific example of solvent 3, an inert solvent such as a perfluorotrialkylamine or a perfluoronaphthalene, or among chlorofluorocarbons, a chlorotrifluoroethylene oligomer (such as Flonrube, tradename) which has a high boiling point among chlorofluorocarbons, is preferred. Further, the amount of solvent 3 is preferably from 10 to 1,000 mass %, based on the compound (4).

Further, in a case where the compound (4) is reacted with a nucleophilic agent or an electrophilic agent for cleavage, such a reaction may be carried out in the absence or presence of a solvent (hereinafter referred to as "solvent 4"). As solvent 4, the same one as solvent 3 is preferred. As the nucleophilic agent, $F^-$ is preferred. Particularly preferred is $F^-$ derived from an alkali metal fluoride. The alkali metal fluoride is preferably NaF, $NaHF_2$, KF or CsF. Among them, NaF is particularly preferred from the viewpoint of economical efficiency.

In a case where a nucleophilic agent (such as $F^-$) is employed, the nucleophilic agent employed at the initial stage of the reaction may be in a catalytic amount or may be in an excess amount. Namely, the amount of the nucleophilic agent such as $F^-$ is preferably from 1 to 500 mol %, more preferably from 1 to 100 mol %, particularly preferably from 5 to 50 mol %, based on the compound (4). The reaction temperature is preferably from −30° C. to the boiling point of the solvent or the compound (4), particularly preferably from −20° C. to 250° C. This method is also preferably carried out by a reaction distillation system.

By the cleavage reaction of compound (4), the ester bond derived from the primary alcohol is cleaved to a —COF residue, and the ester bond derived from the secondary alcohol is cleaved to a —$COR^{1F}$ residue, whereby the ester bond derived from the tertiary alcohol will not change.

Accordingly, by the cleavage reaction of the compound (4), the compound (5) will be formed.

In the process for producing a fluorinated polyvalent carbonyl compound of the present invention, it is possible to obtain the following compound (6) at the same time as the compound (5) by the cleavage of the ester bonds derived from the first and second alcohols in the compound (4). The reaction scheme from the compound (1) to the compound (6) in this case can be represented by the following chemical formulae, provided that the symbols in the following formulae have the same meanings as described above.

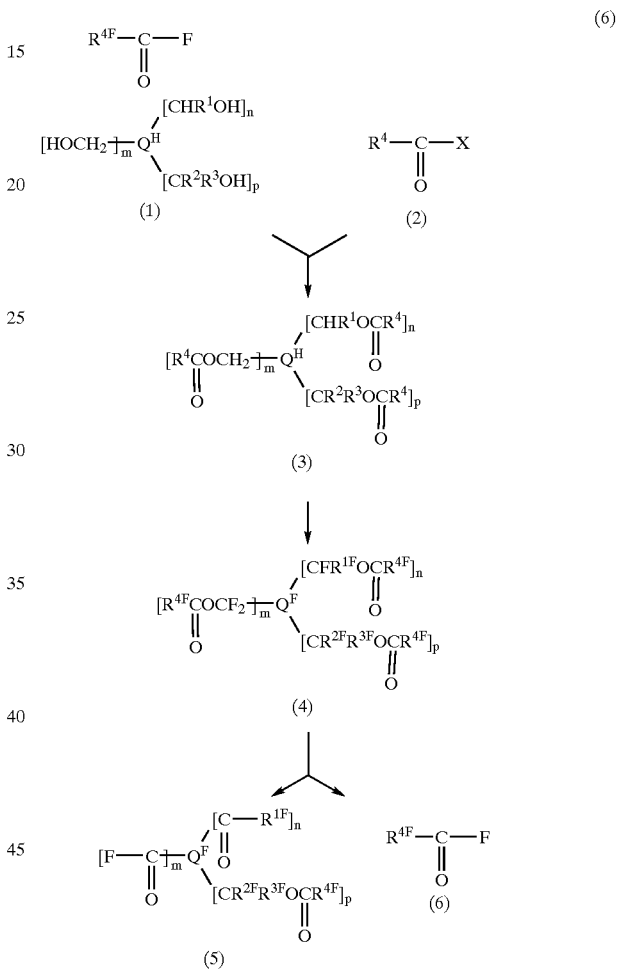

In the present invention, $R^4$ in the compound (2) and $R^{4F}$ in the compound (6) are preferably of the same structure, particularly preferably of the same monovalent perfluorinated saturated organic group. Further, in a case where the compound (2) and the compound (6) are of the same structure, it is possible to produce the compound (5) continuously by using at least a part of the compound (6) obtained from the reaction product obtained by the cleavage of the ester bonds of the compound (4), as at least a part of the compound (2) to be reacted with the compound (1). The reaction scheme of the compound (1), the compound (2) (i.e. the compound (6)), and the compounds (3) to (6) in such a case can be represented by the following chemical formulae.

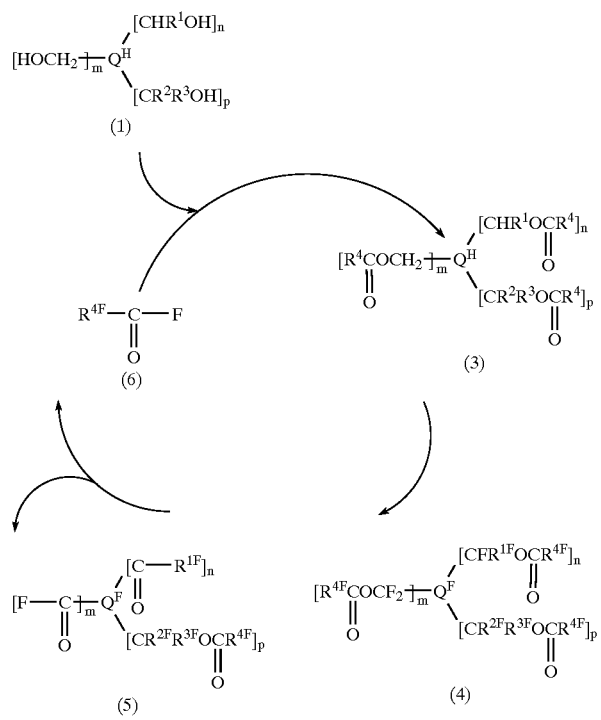

The compound (2) being of the same structure as the compound (6) means that $R^4$ in the compound (2) is $R^{4F}$ in the compound (6), and X in the compound (2) is a fluorine atom. In such a case, the compound (2) will be the same as the compound (6), whereby $R^4$ is $R^{4F}$, and $R^4$ is preferably a monovalent perfluoroalkyl group, a monovalent perfluoro (partially chlorinated) alkyl group, a monovalent perfluoro (etheric oxygen atom-containing alkyl) group or a monovalent perfluoro(partially chlorinated (etheric oxygen atom-containing alkyl)) group. As described in the foregoing, according to the process of the present invention, it is made possible to produce various fluorinated polyvalent carbonyl compounds (compounds (5)) in high yield by a short process by means of the compound (1) and the compound (2) which are materials available at low costs. Further, it is possible to obtain an acid fluoride compound (compound (6)) together with the fluorinated polyhydric carbonyl compound (compounds (5)).

Further, by employing the process of the present invention, it is possible to readily synthesize a fluorinated polyvalent carbonyl compound having a complex structure or a fluorinated polyvalent carbonyl compound having a low molecular weight, which used to be difficult to obtain by conventional methods. Further, the process of the present invention is not limited to the compounds disclosed in Examples, and is a process excellent in common applicability which can be applied to various compounds, whereby a fluorinated polyvalent carbonyl group having a desired skeleton can freely be prepared. Further, the process of the present invention can be made a continuous process, and as solvent 2 to be used in the case of reacting the compound (3) with fluorine in a liquid phase, the compound (6) as a reaction product can be reused. Accordingly, the amounts of the starting materials to be used or the amount of wastes can be reduced, and the fluorinated polyvalent carbonyl compound can be prepared economically very efficiently.

One embodiment of the process of the present invention will be shown in the following reaction scheme. In this reaction scheme, the following compound (10) and the following compound (11) are reacted to obtain the following compound (7), then, the compound (7) is reacted with fluorine in a liquid phase to obtain the following compound (8), and further, the ester bond derived from the primary alcohol in the compound (8) is cleaved to obtain the following compound (9) and the following compound (12). X in the compound (11) represents a halogen atom, and when X is a fluorine atom, the chemical structure will be the same as the compound (12), whereby the compound (9) can be continuously obtained by employing at least a part of the compound (12) as at least a part of the compound (11).

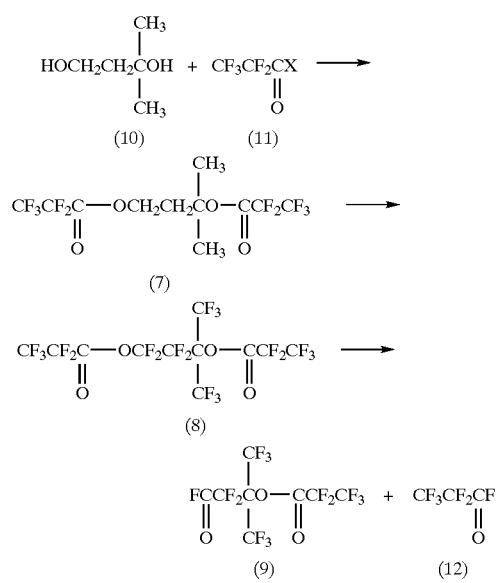

The compound (7), the compound (8) and the compound (9) in the above reaction scheme are novel chemical substances. The compound (9) as one of fluorinated polyvalent carbonyl compounds, is useful as an intermediate for the preparation of various fluorinated compounds, and the compound (7) and the compound (8) are useful as intermediates for the preparation of the compound (9). For example, the compound (9) may be reacted with hexafluoropropylene oxide, followed by pyrolysis to obtain $CF_2=CFO(CF_2)_2C$ $(CF_3)_2OCOCF_2CF_3$, which may further be hydrolyzed to obtain $CF_2=CFO(CF_2)_2C(CF_3)_2OH$. $CF_2=CFO(CF_2)_2C$ $(CF_3)_2OH$ has a hydroxyl group and a polymerizable unsaturated double bond in its molecule and is very useful as a starting material for a functional polymer.

Further, perfluoropyruvic acid fluoride ($CF_3COCOF$) which can be produced by the process of the present invention via the compound (1-1a) and the compound (1-1b), is a compound useful as a base material for pharmaceuticals.

EXAMPLES

Now, the present invention will be described in detail with reference to Examples, but the present invention is by no means thereby restricted. In the following, gas chromatography will be referred to as GC, and gas chromatographic mass analysis will be referred to as GC-MS. Further, the purity obtained from the peak area ratio of GC will be referred to as GC purity, and the yield will be referred to as GC yield. The yield obtained from the peak area ratio of the NMR spectrum will be referred to as yield. Further, tetramethylsilane will be referred to as TMS, $CCl_2FCClF_2$ will be referred to as R-113, and dichloropentafluoropropane manufactured by Asahi Glass Company, Limited will be referred to as AK-225. Further, the NMR spectrum data was shown as an apparent chemical shift range. The standard value for the standard substance $CDCl_3$ in $^{13}C$-NMR was 76.9 ppm. In the quantative analysis by $^{19}F$-NMR, $C_6F_6$ was employed as an internal standard.

Example 1

Example 1-1:
Example for Esterification Step $CH_2Cl_2$ (509 g), pyridine (177 g) and $HOC(CH_3)_2CH_2CH_2OH$ (20 g) were put into a flask and stirred while bubbling nitrogen gas. $CF_3CF_2COF$ (72 g) was fed over a period of two hours while maintaining the internal temperature at a level of from $-5°$ C. to $+4°$ C. After completion of the feeding, the reaction crude liquid was dropwise added to a 5 mass % hydrochloric acid aqueous solution (1,400 g) while maintaining the internal temperature at a level of at most 2° C. After liquid separation, washing with a hydrochloric acid aqueous solution was further carried out, followed by liquid separation to obtain an organic layer (500 g). Further, the organic layer was washed with a 5 mass % sodium hydrogencarbonate solution (470 g), and subjected to liquid separation, whereupon the organic layer was washed with water (520 ml) and dried over magnesium sulfate, followed by filtration to obtain a crude liquid (450 g). The crude liquid was concentrated by an evaporator and then distilled under reduced pressure to obtain a fraction (47 g) of 61° C./0.3 kPa. This fraction was purified by silica gel column chromatography (developing solvent: AK-225) to obtain a purified product (43.1 g). The GC purity was 98%. From the NMR spectrum, it was confirmed that the following compound (7) was the main component. Further, the NMR spectrum data were as shown below.

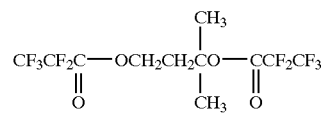

$^1H$-NMR (399.0 MHz, solvent: $CDCl_3$, standard: TMS) δ (ppm): 1.64 (s, 6H), 2.31 (t, J=6.6 Hz, 2H), 4.51 (t, J=6.6 Hz, 2H).
$^{19}F$-NMR (376.0 MHz, solvent: $CDCl_3$, standard: $CFCl_3$) δ (ppm): −83.8 (6F), −122.5 (4F).

Example 1-2
Example for Fluorination Step

Into a 200 mL nickel autoclave, R-113 (156 g) was added, stirred and maintained at 25° C. At the gas outlet of the autoclave, a cooler maintained at −10° C. and a pressure controlling bulb were installed in series. Nitrogen gas was supplied for one hour. Then, fluorine gas diluted to 20% by nitrogen gas was supplied at a flow rate of 5.77 L/hr for one hour, and the internal pressure of the reactor was adjusted to 0.15 MPa. Then, diluted fluorine gas was supplied at the same flow rate, and while adjusting the internal pressure of the reactor to 0.15 MPa, a solution obtained by dissolving the compound (7) (4.01 g) obtained in the esterification step, in R-113 (80 g), was injected over a period of 5.8 hours.

Then, diluted fluorine gas was supplied at the same flow rate, and while adjusting the internal pressure of the reactor to 0.15 MPa, a benzene/R-113 solution having a concentration of 0.01 g/mL was injected in an amount of 6 ml while raising the temperature from 25° C. to 40° C., whereupon stirring was continued for 0.2 hour. Then, diluted fluorine gas was supplied at the same flow rate, and while maintaining the internal temperature of the reactor at 40° C. and the internal pressure of the reactor at 0.15 MPa, the above-mentioned benzene solution (3 ml) was injected, whereupon stirring was continued for 0.2 hour. Further, the same operation was repeated five times. The total amount of benzene injected was 0.245 g, and the total amount of R-113 injected was 24 ml. Further, diluted fluorine gas was supplied for one hour, and nitrogen gas was supplied for 1.5 hours. The yield by $^{19}F$-NMR of the obtainer compound was 49%. Further, from the results of $^{19}F$-NMR, the obtained compound was found to be the following compound (8). The NMR spectrum data were as follows.

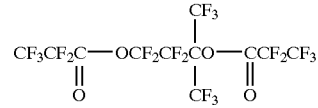

$^{19}F$-NMR (376.0 MHz, solvent: $CDCl_3$, standard: $CFCl_3$) δ (ppm): −67.3 (6F), −67.5 (2F), −83.1 (3F), −83.2 (3F), −116.1 (2F), −121.1 (2F), −122.2 (2F).

Example 1-3
Example for Step for Cleavage of Ester Bonds

The compound (8) (0.5 g) obtained in the fluorination step was charged into a flask together with NaF powder (0.02 g) and heated at 100° C. for 3.5 hours and at 120° C. for 2.5 hours, in an oil bath while vigorously stirring. At the upper portion of the flask, a reflux condenser having the temperature adjusted at 20° C. and a gas sampling bag were disposed in series. After cooling, a liquid sample (0.4 g) and a gas sample (0.1 g) were recovered. As a result of the analysis by GC-MS, in the liquid sample, the following compound (9) was confirmed to be the main product, and in the gas sample, $CF_3CF_2COF$ was confirmed to be the main product. The yield of the compound was obtained by NMR and found to be 44.0%. Further, the NMR spectrum data were as follows.

$^{19}$F-NMR (376.0 MHz, solvent: $CDCl_3$, standard: $CFCl_3$) δ (ppm): 23.4 (1F), −68.2 (6F), −83.1 (3F), −108.5 (2F), −121.3 (2F).

Example 2

Example 2-1

Example for Production of $CH_3CH[OCOCF(CF_3)OCF_2CF(CF_3)OCF_2CF_2CF_3]CH_2OCOCF(CF_3)OCF_2CF(CF_3)OCF_2CF_2CF_3$ by Esterification Reaction $CH_3CH(OH)CH_2OH$ (10.0 g) was put into a flask and stirred while bubbling nitrogen gas. $FCOCF(CF_3)OCF_2CF(CF_3)OCF_2CF_2CF_3$ (137.6 g) was dropwise added over a period of 40 minutes, while maintaining the internal temperature at from 28 to 30° C. After completion of dropwise addition, stirring was carried out for 7 hours while maintaining the internal temperature at 30° C., and 150 ml of a saturated sodium hydrogencarbonate aqueous solution was added at an internal temperature of at most 15° C.

The obtained crude liquid was subjected to liquid separation to obtain a fluorocarbon layer. Further, the fluorocarbon layer was washed twice with 50 ml of water, dried over magnesium sulfate and then filtered to obtain a crude liquid. The crude liquid was purified by silica gel column chromatography (developing solvent: AK-225) to obtain the above identified compound (73.1 g), the formed product. The purity by GC was 99%. The NMR spectrum data were as follows.

$^3$H-NMR (300.4 MHz, solvent: $CDCl_3$, standard: $CHCl_3$) δ (ppm): 1.39 to 1.45 (m, 3H), 4.28 to 4.70 (m, 2H), 5.35 to 5.47 (m, 1H).

$^{19}$F-NMR (282.7 MHz, solvent: $CDCl_3$, standard: $CFCl_3$) δ (ppm): −78.6 to −85.2 (26F), −129.5 (4F), −131.6 (2F), −145.1 (2F).

Example 2-2

Example for Production of $CF_3CF[OCOCF(CF_3)OCF_2CF(CF_3)OCF_2CF_2CF_3]CF_2OCOCF(CF_3)OCF_2CF(CF_3)OCF_2CF_2CF_3$ by Fluorination Reaction Into a 500 cc nickel autoclave, R-113 (313 g) was added, stirred and maintained at 25° C. At the gas outlet of the autoclave, a cooler maintained at 20° C., a layer packed with NaF pellets and a cooler maintained at −10° C., were installed in series. Further, a liquid returning line to return the condensed liquid from the cooler maintained at −10° C. to the autoclave, was installed. Nitrogen gas was supplied for 1.0 hour and then, fluorine gas diluted to 20% by nitrogen gas, was supplied at a flow rate of 7.28 L/hr, and the internal pressure of the reactor was maintained at 0.15 MPa. Then, while supplying fluorine gas diluted to 20% by nitrogen gas, at the same flow rate and while maintaining the internal pressure of the reactor at 0.15 MPa, a solution obtained by dissolving the product (50.3 g) obtained in Example 2-1 in R-113 (250 g), was injected over a period of 8.3 hours.

Then, while supplying fluorine gas diluted to 20% by nitrogen gas at the same flow rate and while maintaining the pressure of the reactor at 0.15 MPa, a R-113 solution having a benzene concentration of 0.01 g/ml, was injected in an amount of 9 ml while raising the temperature from 25° C. to 40° C., whereupon the benzene injection inlet of the autoclave was closed, and stirring was continued for 0.3 hour. Then, while maintaining the pressure of the reactor at 0.15 MPa and the internal temperature of the reactor at 40° C., the above benzene solution was injected in an amount of 6 ml, and stirring was continued for 0.3 hour. The same operation was repeated ten times, and further stirring was continued for 0.7 hour. The total amount of benzene injected was 0.76 g, and the total amount of 1,1,2-trichlorotrifluoroethane injected was 75 ml. Further, nitrogen gas was supplied for 1.0 hour. The formed product was quantatively analyzed by $^{19}$F-NMR (internal standard: $C_6F_6$), whereby the yield of the above identified compound was 81%.

$^{19}$F-NMR (376.0 MHz, solvent: $CDCl_3$, standard: $CFCl_3$) δ (ppm): −77.6 (2F), −78.5 to −87.6 (29F), −130.1 (4F), −132.1 (2F), −142.2 to −144.5 (1F), −145.2 to −147.1 (2F).

Example 2-3

Example for Production of $CF_3COCOF$ by Liquid Phase Pyrolysis

The formed product obtained in Example 2-2 (42.0 g) was charged into a 200 cc autoclave together with KF powder (0.5 g) and $CF_3CFHOCF_2CF(CF_3)OCF_2CF_2CF_3$ and heated in a sealed state at from 80 to 120° C. for 13 hours and 120° C. for 14 hours in an oil bath, while vigorously stirring. At the outlet of the autoclave, a pressure resistant container cooled to −78° C. was installed, and when the internal pressure of the reactor became at least 0.28 MPa, the gas in the reactor was liquefied and recovered. 0.8 g of a sample was recovered. The recovered sample was gaseous at room temperature, and as a result of the analysis by GC-MS, the above-identified compound was confirmed to be the main product. The yield of the above-identified compound was 9.4%.

INDUSTRIAL APPLICABILITY

As described in the foregoing, by the present invention, a fluorinated polyvalent carbonyl compound can be produced by an economically advantageous process from inexpensive materials without requiring a complicated synthetic step.

The entire disclosure of Japanese Patent Application No. 2000-294801 filed on Sep. 27, 2000 including specification, claims and summary is incorporated herein by reference in its entirety.

What is claimed is:

1. A fluorinated polyvalent carbonyl compound selected from the group consisting of a compound of the following formula (7), a compound of the following formula (8), a compound of the following formula (9), a compound of the following formula (1-1a), and a compound of the following formula (1-1b):

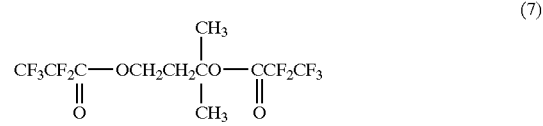

-continued

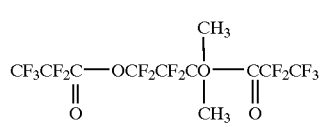  (8)

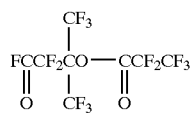  (9)

  (1-1a)

  (1-1b).

2. The fluorinated polyvalent carbonyl compound according to claim 1, wherein the fluorinated polyvalent carbonyl compound is the compound of the formula (7).

3. The fluorinated polyvalent carbonyl compound according to claim 1, wherein the fluorinated polyvalent carbonyl compound is the compound of the formula (8).

4. The fluorinated polyvalent carbonyl compound according to claim 1, wherein the fluorinated polyvalent carbonyl compound is the compound of the formula (9).

5. The fluorinated polyvalent carbonyl compound according to claim 1, wherein the fluorinated polyvalent carbonyl compound is the compound of the formula (1–1a).

6. The fluorinated polyvalent carbonyl compound according to claim 1, wherein the fluorinated polyvalent carbonyl compound is the compound of the formula (1–1b).

* * * * *